United States Patent [19]
Chenard

[11] Patent Number: 6,136,861
[45] Date of Patent: Oct. 24, 2000

[54] BICYCLO[2.2.1]HEPTANES AND RELATED COMPOUNDS

[75] Inventor: Bertrand Leo Chenard, Waterford, Conn.

[73] Assignee: Pfizer Inc, New York, N.Y.

[21] Appl. No.: 09/380,727

[22] PCT Filed: Mar. 4, 1999

[86] PCT No.: PCT/IB99/00376

§ 371 Date: Sep. 7, 1999

§ 102(e) Date: Sep. 7, 1999

[87] PCT Pub. No.: WO99/47490

PCT Pub. Date: Sep. 23, 1999

Related U.S. Application Data

[60] Provisional application No. 60/078,346, Mar. 17, 1998.

[51] Int. Cl.$^7$ .......................... A61K 31/195; C07C 61/12
[52] U.S. Cl. ........................... 514/561; 562/500; 562/502
[58] Field of Search .................................. 562/500, 502; 514/561

[56] References Cited

U.S. PATENT DOCUMENTS 5,587,398 12/1996 Elmaleh et al. .

FOREIGN PATENT DOCUMENTS 696577 2/1996 European Pat. Off. .

OTHER PUBLICATIONS

D. D. Schoepp et al.: "3,5–Dihydroxyphenylglycine Is a Highly Selective Agonist for Phosphoinositide–Linked Metabotropic Glutamate Receptors in the Rat Hippocampus"; *Journal of Neurochemistry*, vol. 63, No. 2, 1994, pp. 769–772.

D. D. Schoepp et al.: "Inhibition of Cyclic AMP Formation by a Selective Metabotropic Glutamate Receptor Agonist"; *Journal of Neurochemistry*, vol. 58, No. 3, 1992, pp. 1184–1186.

Y. Nakagawa et al.: "(2S,3S,4S) α–(Carboxycyclopropyl)glycine is a novel agonist of metabotropic glutamate receptors"; *European Journal of Pharmacology*, 184 (1990), pp. 205–206.

D. D. Schoepp et al: "Comparison of (1S,3R)–1–aminocyclopentane–1,3–dicarboxylic acid (1S,3R-ACPD)—and 1R,3S-ACPD-stimulated brain phosphoinositide hydrolysis"; *European Journal of Pharmacology—Molecular Pharmacology Section*, 207 (1991), pp. 351–353.

Y. Hayashi et al.; "Agonist analysis of 2–(carboxycyclopropyl)glycine isomers for cloned metabotropic gluatamate receptor subtypes expressed in Chinese hamster ovary cells"; *Br. J. Pharmacol.* (1992), 107, pp. 539–543.

D. D. Schoepp et al.; "Metabotropic glutamate receptors in brain function and pathology"; *TiPS*, Jan. 1993 [vol. 14], pp. 13–20.

J. C. Watkins et al.; "Structure–activity relationships in the development of excitatory amino acid receptor agonists and competitive antagonists"; *TiPS*, Jan. 1990 [vol. 11], pp. 25–33.

J. W. McDonald et al; "Physiological and pathophysiological roles of excitatory amino acids during central nervous system development"; *Brain Research Reviews*, 15, (1990), pp. 41–70.

D. D. Schoepp et al.; "Pharmacological and functional characteristics of metabotropic excitatory amino acid receptors"; *TiPS*, Dec. 1990 [vol. 11], pp. 508–515.

D. T. Monaghan et al; "The Excitatory Amino Acid Receptors: Their Classes, Pharmacology, and Distinct Properties in the Function of the Central Nervous System"; *Annu. Rev. Pharmacol. Toxicol.*, 1989, 29: pp. 365–402.

J. C. Watkins et al.: "Excitatory Amino Acid Transmitters"; *Annu. Rev. Pharmacol. Toxicol.*, 1981, 21, pp. 165–204.

*Primary Examiner*—Gary Geist
*Assistant Examiner*—Leigh C. Maier
*Attorney, Agent, or Firm*—P. C. Richardson; P. H. Ginsburg; Israel Nissenbaum

[57] ABSTRACT

The present invention relates to compounds of the formula I, as defined in the specification, pharmaceutical compositions containing such compounds the use of such compounds to treat neurological and psychiatric disorders.

23 Claims, No Drawings

BICYCLO[2.2.1]HEPTANES AND RELATED COMPOUNDS

This Application claims the benefit of U.S. Provisional Application Ser. No. 60/078,346, filed Mar. 17, 1998. This application is a 371 of PCT/IB99/00376 filed Mar. 4, 1996.

Background of the Invention

The present invention relates to compounds of the formula 1, as described below, their pharmaceutically acceptable salts, pharmaceutical compositions containing them and their use in treating neurological and psychiatric disorders.

The role of excitatory amino acids, such as glutamic acid and aspartic acid, as the predominant mediators of excitatory synaptic transmission in the central nervous system has been well established. Watkins & Evans, *Ann. Rev. Pharmacol. Toxicol.*, 21, 165 (1981); Monaghan, Bridges, and Cotman, *Ann. Rev. Pharmacol. Toxicol.*, 29, 365 (1989); Watkins, Krogsgaard-Larsen, and Honore, *Trans. Pharm. Sci.*, 11, 25 (1990). These amino acids function in synaptic transmission primarily through excitatory amino acid receptors. These amino acids also participate in a variety of other physiological processes such as motor control, respiration, cardiovascular regulation, sensory perception, and cognition.

Excitatory amino acid receptors are classified into two general types. Receptors that are directly coupled to the opening of cation channels in the cell membrane of the neurons are termed "ionotropic." This type of receptor has been subdivided into at least three subtypes, which are defined by the depolarizing actions of the selective agonists N-methyl-D-aspartate (NMDA), α-amino-3-hydroxy-5-methylisoxazole4-propionic acid (AMPA), and kainic acid (KA). The second general type is the G-protein or second messenger-linked "metabotropic" receptor. This second type, when activated by the agonists quisqualate, ibotenate, or trans-1-aminocyclopentane-1,3-dicarboxylic acid or 2-amino4-phosphonobutyric acid activates second messenger systems. A subset of these second messenger-linked recptors is negatively coupled to adenylate cyclase. Both types of receptors appear not only to mediate normal synaptic transmission along excitatory pathways, but also participate in the modification of synaptic connection during development and changes in the efficiency of synaptic transmission throughout life. Schoepp, Bockaert, and Sladeczek. *Trends in Pharmacol. Sci.*, 11, 508 (1990); McDonald and Johnson, *Brain Research Reviews*, 15, 41 (1990).

The excessive or inappropriate stimulation of excitatory amino acid receptors leads to neuronal cell damage or loss by way of a mechanism known as excitotoxicity. This process has been suggested to mediate neuronal degeneration in a variety of conditions. The medical consequences of such neuronal degeneration makes the abatement of these degenerative neurological processes an important therapeutic goal.

Excitatory amino acid excitotoxicity has been implicated in the pathophysiology of a number of neurological disorders. This excitotoxicity has been implicated in the pathophysiology of acute and chronic neurodegenerative conditions including stroke, cerebral ischemia, spinal cord trauma, head trauma, Alzheimer's Disease, Huntington's Chorea, amyotrophic lateral sclerosis, epilepsy, AIDS-induced dementia, perinatal hypoxia, hypoxia (such as conditions caused by strangulation, surgery, smoke inhalation, asphyxiation, drowning, choking, electrocution or drug or alcohol overdose), cardiac arrest, hypoglycemic neuronal damage, ocular damage and retinopathy, idiopathic and drug-induced Parkinson's Disease and cerebral deficits subsequent to cardiac bypass surgery and grafting. Other neurological conditions that are caused by glutamate dysfunction require neuromodulation. These other neurological conditions include muscular spasms, migraine headaches, urinary incontinence, psychosis, addiction withdrawal (such as alcoholism and drug addiction including opiate, cocaine and nicotine addiction), opiate tolerance, anxiety, emesis, brain edema, chronic and acute pain, convulsions, retinal neuropathy, tinnitus and tardive dyskinesia. The use of a neuroprotective agent, such as an AMPA receptor antagonist, is believed to be useful in treating these disorders and/or reducing the amount of neurological damage associated with these disorders. The excitatory amino acid receptor (EAA) antagonists are also believed to be useful as analgesic agents.

The metabotropic glutamate receptors are a highly heterogeneous family of glutamate receptors that are linked to multiple second-messenger pathways. Generally, these receptors function to modulate the presynaptic release of glutamate, and the postsynaptic sensitivity of the neuronal cell to glutamate excitation. The metabotropic glutamate receptors (mGluR) have been pharmacologically divided into three subtypes. One group of receptors ("Class I receptors") is positively coupled to phospholipase C, which causes hydrolysis of cellular phosphoinositides (PI). This first group are termed PI-linked metabotropic glutamate receptors. The second group of receptors ("Class II and Class III receptors") is negatively coupled to adenylate cyclase, which prevents the forskolin-stimulated accumulation of cyclic adenosine monophosphate (cAMP). Schoepp and Conn, *Trends Pharmacol. Sci.*, 14, 13 (1993). Class II and Class III receptors are distinquished by selective activation with trans-1-aminocyclopentane-1,3-dicarboxylic acid and 2-amino-4-phosphonobutyric acid, respectively. Receptors within this second group are termed cAMP-linked metabotropic glutamate receptors. Agonists of the cAMP-linked metabotropic glutamate receptors should be useful for the treatment of acute and chronic neurological conditions and psychiatric conditions.

Compounds have recently been discovered that effect metabotropic glutamate receptors, but have no effect on ionotropic glutamate receptors. (1S,3R)-1-Aminocyclopentane- 1,3-dicarboxylic acid (1S,3R-ACPD) is an agonist of PI-linked and cAMP-linked metabotropic glutamate receptors. Schoepp, Johnson, True, and Monn., *Eur. J. Pharmacol.*, 207, 351 (1991); Schoepp, Johnson, and Monn, *J. Neurochem.*, 58, 1184 (1992). (2S,3S,4S)-2-(carboxycyclopropyl) glycine (L-CCG-1) was recently described as a selective cAMP-linked metabotropic glutamate receptor agonist: however, at higher concentrations, this compound has activity at PI-linked metabotropic receptors. Nakagawa, et al., *Eur J. Pharmacol.*, 184, 205 (1990): Hayashi, et al., *Br. J. Pharmacol.*, 197, 539 (1992): Schoepp et al.,*J. Neurochem.*, 63., 769–772 (1994).

European Patent Application EP 696577A1, which was published on Feb. 14, 1996, refers to certain synthetic amino acids that are described as being selective for the negatively coupled cAMP linked metabotropic glutamate receptors (i.e., Class II metabotropic glutamate receptors).

The compounds of formula I and their pharmaceutically acceptable salts are metabotropic glutamate receptor ligands that are selective for Class II metabotropic glutamate receptors.

SUMMARY OF THE INVENTION

This invention relates to compounds of the formula

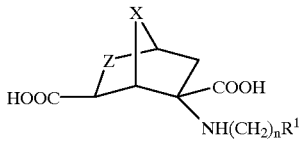

I wherein n is 0–6;

X is $CH_2$, $CH_2CH_2$ or oxygen;

Z is $CHR^2$ or $NR^2$; and $R^1$ and $R^2$ are selected independently, from hydrogen, $(C_1-C_6)$alkyl, aryl and heteroaryl, wherein said aryl is selected from phenyl and naphthyl and said heteroaryl is selected from 5 and 6 membered aromatic heterocyclic rings that contain from one to four heteroatoms selected, independently, from nitrogen, oxygen and sulfur, and wherein said aryl and heteroaryl moieties can optionally be substituted with one or more substituents, preferably with one or two substituents, that are selected, independently, from halo (e.g., fluoro, chloro, bromo or iodo), $-S(C_1-C_6)$alkyl, $-S(O)(C_1-C_6)$alkyl, $-S(O)_2(C_1-C_6)$alkyl, $(C_1-C_6)$alkyl optionally substituted with from one to seven fluorine atoms, $(C_1-C_6)$alkoxy optionally substituted with from one to seven fluorine atoms, amino, nitro, cyano, carboxy, $-CO_2(C_1-C_6)$alkyl, $(C_1-C_6)$alkylamino, di-$[(C_1-C_6)$alkyl]amino phenoxy, anilino and phenylthio;

with the proviso that none of the foregoing heteroaryl moieties may contain more than one ring oxygen atom or more than one ring sulfur atom;

and the pharmaceutically acceptable salts of such compounds.

Examples of the heteroaryl moieties of said heteroaryl-$(C_0-C_6)$alkyl are the following: oxazolyl, isoxazoyl, thiazolyl, isothiazolyl, furanyl, pyrazolyl, pyrrolyl, tetrazolyl, triazolyl, thienyl, imidazolyl, pyridinyl, and pyrimidinyl.

This invention also relates to compounds of the formulas and

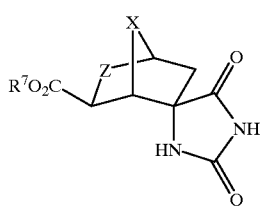

II

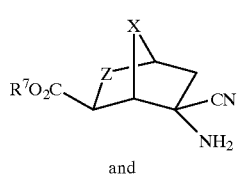

III and

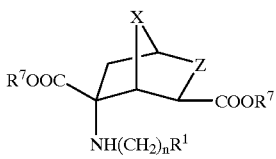

IV wherein X and Z are defined as for formula I above and $R^7$ is hydrogen, $(C_1-C_6)$alkyl or benzyl.

Compounds of the formula II, III and IV are intermediates in the synthesis of compounds of the formula I.

Preferred compounds of the formula I include those wherein $R^1$ is a pyrid-3-yl or pyrid-4-yl group.

Other preferred compounds of formula I include those wherein $R^1$ is hydrogen, unsubstituted phenyl, or phenyl substituted with one or two substitutents. When $R^1$ is a substituted phenyl, preferred substitutents on said phenyl are independently selected from $(C_1-C_6)$alkyl, nitro, cyano, halo, $CF_3$, $(C_1-C_5)$alkyl substituted with $CF_3$, $(C_1-C_5)$ alkoxy substituted with $CF_3$, and $-O-CF_3$.

Other preferred compounds of the formula I include those wherein n is 1–6. Compounds of formula 1 wheren n is 1 or 2 are more preferred.

Other preferred compounds of formula I include those wherein Z is $CH_2$.

Other preferred compounds of formula 1 include those wherein X is $CH_2$.

Other preferred compounds of formula I include those wherein both X and Z are $CH_2$, $R^1$ is hydrogen and n is zero.

Other embodiments of this invention include compounds of the formula I wherein:

(a) Z is NH;

(b) Z is NR and $R^2$ is $(C_1-C_6)$alkyl;

(c) Z is $NR^2$ and $R^2$ is phenyl;

(d) Z is $NR^2$, n is zero and $R^1$ is phenyl or substituted phenyl;

(e) one of $R^1$ and R is aryl or heteroaryl; or (f) both $R^1$ and $R^2$ are selected from aryl, subtituted aryl, heteroaryl and substituted heteroaryl.

Preferred compounds of formula I include, but are not limited to:

2-(endo)-amino-bicyclo[2.2.1]heptane-2-(exo)—(exo)-dicarboxylic acid;

(+)-2-(endo)-aminobicyclo[2.2.1]heptane-2-(exo)-6-(exo)-dicarboxylic acid;

(−)-2-(endo)-aminobicyclo[2.2.1]heptane-2-(exo)-6-(exo)-dicarboxylic acid;

2-(endo)-benzylamino-bicyclo[2.2.1]heptane-2-(exo)-6-(exo)-dicarboxylic acid; and 2-(endo)-phenylethylami no-bicyclo[2.2.1]heptane-2-(exo)-6-(exo)-dicarboxylate.

Preferred compounds of formulas II, III, and IV include those wherein $R^7$ is hydrogen, $(C_1-C_6)$alkyl, or benzyl. In one embodiment, a compound of formula II, III, or IV includes $R^7$, wherein $R^7$ is $(C_1-C_6)$ t-alkyl, for example t-butyl.

The compounds of formula I and their pharmaceutically acceptable salts are metabotropic glutamate receptor ligands and are useful in the treatment of a variety of neurological and psychiatric disorders. Examples of neurological disorders that can be treated with the compounds of formula I and their pharmaceutically acceptable salts are cerebral deficits subsequent to cardiac bypass surgery and grafting, cerebral ischemia (e.g., stroke and cardiac arrest), spinal cord trauma, head trauma, Aizheimer's Disease, Huntington's disease, amyotrophic lateral sclerosis, AIDS-induced dementia, muscular spasms, migrane headache, urinary incontinence, convulsions, perinatal hypoxia, hypoglycemic neuronal damage, chemical dependencies and addictions (e.g., a dependency on, or addiction to opiates, benzodiazepines, cocaine, nicotine or ethanol), drug or alcohol withdrawal symptoms, ocular damage and retinopathy, cognitive disorders, idiopathic and drug-induced Parkinson's Disease, emesis, brain edema, acute or chronic pain, sleep disorders, Tourette's syndrome, attention deficit disorder and tardive dyskinesia. Examples of psychiatric disorders that can be treated with the compounds of formula I and their pharamaceutically acceptable salts are schizophrenia, anxiety and related disorders (e.g., General Anxiety Disorder, panic attack and stress-related disorders such as Post Traumatic Stress Syndrome), depression, bipolar disorders, psychosis, and obsessive compulsive disorders.

The present invention also relates to the pharmaceutically acceptable acid addition salts of compounds of the formula I. The acids which are used to prepare the pharmaceutically acceptable acid addition salts of the aforementioned base compounds of this invention are those which form non-toxic acid addition salts, i.e., salts containing pharmacologically acceptable anions, such as the hydrochloride, hydrobromide, hydroiodide, nitrate, sulfate, bisulfate, phosphate, acid phosphate, acetate, lactate, citrate, acid citrate, tartrate, bitartrate, succinate, maleate, fumarate, gluconate, saccharate, benzoate, methanesulfonate, ethanesulfonate, benzenesulfonate, p-toluenesulfonate and pamoate [i.e., 1,1'-methylene-bis-(2-hydroxy-3-naphthoate)]salts.

The present invention also relates to the pharmaceutically acceptable base addition salts of compounds of the forumula I. These salts are all prepared by conventional techniques. The chemical bases that are used as reagents to prepare the pharmaceutically acceptable base salts of this invention are those which form non-toxic base salts with the acidic compounds of formula I. Such non-toxic base salts include those derived from such pharmacologically acceptable cations as sodium, potassium, calcium and magnesium, etc.

This invention also relates to a pharmaceutical composition for treating a disorder or condition, the treatment or prevention of which can be effected or facilitated by modulating (i.e., increasing or decreasing) glutamate neurotransmission in a mammal, comprising an amount of a compound of the formula I, or a pharmaceutically effective salt thereof, that is effective in treating such disorder or condition and a pharmaceutically acceptable carrier.

This invention also relates to a method of treating a disorder or condition, the treatment of which can be effected or facilitated by modulating glutamate neurotransmission in a mammal, comprising administering to a mammal in need of such treatment an amount of a compound of the formula I, or a pharmaceutically effective salt thereof, that is effective in treating such disorder or condition.

This invention also relates to a pharmaceutical composition for treating a condition selected from stroke, cerebral ischemia, spinal cord trauma, head trauma, Alzheimer's Disease, Huntington's Chorea, amyotrophic lateral sclerosis, epilepsy, AIDS-induced dementia, muscular spasms, migraine headaches, urinary incontinence, psychosis, convulsions, perinatal hypoxia, hypoxia (such as conditions caused by strangulation, surgery, smoke inhalation, asphyxiation, drowning, choking, electrocution or drug or alcohol overdose), cardiac arrest, hypoglycemic neuronal damage, chemical dependencies and addictions (e.g., addictions to or dependencies on alcohol, opiates, benzodiazepines, nicotine, heroin or cocaine), ocular damage, retinopathy, retinal neuropathy, tinnitus, idiopathic and drug induced Parkinson's Disease, anxiety (e.g., Post Traumatic Stress Syndrome, panic disorder, General Anxiety Disorder, simple phobias and social phobias), schizophrenia, depression, bipolar disorder, obsessive-compulsive disorder, Tourette's syndrome, emesis, brain edema, chronic and acute pain, tardive dyskinesia and cerebral deficits subsequent to cardiac bypass surgery and grafting in a mammal, comprising a glutamate neurotransmission modulating effective amount of a compound of the formula 1, or a pharmaceutically salt thereof, and a pharmaceutically acceptable carrier.

This invention also relates to a method for treating a condition selected from stroke, cerebral ischemia, spinal cord trauma, head trauma, Alzheimees Disease, Huntington's Chorea, amyotrophic lateral sclerosis, epilepsy, AIDS-induced dementia, muscular spasms, migraine headaches, urinary incontinence, psychosis, convulsions, perinatal hypoxia, hypoxia (such as conditions caused by strangulation, surgery, smoke inhalation, asphyxiation, drowning, choking, electrocution or drug or alcohol overdose), cardiac arrest, hypoglycemic neuronal damage, chemical dependencies and addictions (e.g., addictions to or dependencies on alcohol, opiates, benzodiazepines, nicotine, heroin or cocaine), ocular damage, retinopathy, retinal neuropathy, tinnitus, idiopathic and drug induced Parkinson's Disease, anxiety (e.g., panic disorder, Post Traumatic Stress Syndrome, General Anxiety Disorder, simple phobias and social phobias), schizophienia, depression, bipolar disorder, obsessive-compulsive disorder, Tourette's syndrome, emesis, brain edema, chronic and acute pain, tardive dyskinesia and cerebral deficits subsequent to cardiac bypass surgery and grafting in a mammal, comprising administering to a mammal requiring such treatment a glutamate neurotransmission modulating effective amount of a compound of the formula I, Ior a pharmaceutically acceptable salt thereof.

This invention also relates to a pharmaceutical composition for treating a disorder or condition, the treatment of which can be effected or facilitated by modulating glutamate neurotransmission in a mammal, comprising a glutamate neurotransmission modulating effective amount of a compound of the formula I, or a pharmaceutically acceptable salt thereof, and a pharmaceutically acceptable carrier.

This invention also relates to a method for treating a disorder or condition, the treatment of which can be effected or facilitated by modulating glutamate neurotransmission in a mammal, comprising administering to a mammal requiring such treatment a glutamate neurotransmission modulating effective amount of a compound of the formula I or a pharmaceutically acceptable salt thereof. This invention also relates to a method of treating a condition selected from stroke, cerebral ischemia, spinal cord trauma, head trauma, Alzheimer's Disease, Huntington's Chorea, amyotrophic lateral sclerosis, epilepsy, AIDS-induced dementia, muscular spasms, migraine headaches, urinary incontinence, psychosis, convulsions, perinatal hypoxia, hypoxia (such as conditions caused by strangulation, surgery, smoke inhalation, asphyxiation, drowning, choking, electrocution or drug or alcohol overdose), cardiac arrest, hypoglycemic neuronal damage, chemical dependencies and addictions (e.g., addictions to or dependencies on alcohol, opiates, benzodiazepines, nicotine, heroin or cocaine), ocular damage, retinopathy, retinal neuropathy, tinnitus, idiopathic and drug induced Parkinson's Disease, anxiety (e.g., panic disorder, Post traumatic Stress Syndrome, General Anxiety disorder, simple phobias and social phobias), schizophienia, depression, bipolar disorder, obsessive-compulsive disorder, Tourette's syndrome, emesis, brain edema, chronic and acute pain, tardive dyskinesia and cerebral deficits subsequent to cardiac bypass surgery and grafting in a mammal, comprising administering to a mammal in need of such treatment an amount of a compound of the formula I that is effective in treating such condition.

This invention also relates to a pharmaceutical composition for treating a condition selected from stroke, cerebral ischemia, spinal cord trauma, head trauma, Alzheimer's Disease, Huntington's Chorea, amyotrophic lateral sclerosis, epilepsy, AIDS-induced dementia, muscular spasms, migraine headaches, urinary incontinence, psychosis, convulsions, perinatal hypoxia, hypoxia (such as conditions caused by strangulation, surgery, smoke inhalation, asphyxiation, drowning, choking, electrocution or drug or alcohol overdose), cardiac arrest, hypoglycemic neuronal damage, chemical dependencies and addictions (e.g., addictions to or dependencies on alcohol, opiates, benzodiazepines, nicotine, heroin or cocaine), ocular damage, retinopathy, retinal neuropathy, tinnitus, idiopathic and drug induced Parkinson's Disease, anxiety (e.g., panic disorder, Post Traumatic Stress Syndrome, General Anxiety Disorder, simple phobias and social phobias), schizophienia, depression, bipolar disorder, obsessive-compulsive disorder, Tourette's syndrome, emesis, brain edema, chronic and acute pain, tardive dyskinesia and cerebral deficits subsequent to cardiac bypass surgery and grafting in a mammal, comprising an amount of a compound of the formula I that is effective in treating such condition and a pharmaceutically acceptable carrier.

This invention also relates to a method for treating a disorder or condition, the treatment of which can effected or facilitated by modulating glutamate neurotransmission in a mammal, comprising administering to a mammal requiring such treatment:

(a) a compound of the formula 1, or a pharmaceutically acceptable salt thereof; and (b) a serotonin reuptake inhibitor (e.g., sertraline, fluoxetine, fluvoxamine, paroxetine, citalopram, fenfluramine, femoxetine, etc.) or a serotonin-1A ($5HT_{1A}$) receptor ligand (e.g., buspirone, flesinoxan, etc.) or a pharmaceutically acceptable salt of such inhibitor or ligand;

wherein the amounts of the compound of formula I and the serotonin reuptake inhibitor or $5HT_{1A}$ receptor ligand that are employed in such method are such that the combination of the two active ingredients is effective in treating such disorder or condition.

This invention also relates to a pharmaceutical composition for treating a disorder or condition, the treatment of which can effected or facilitated by modulating glutamate neurotransmission in a mammal, comprising:

(a) a compound of the formula I, or a pharmaceutically acceptable salt thereof;

(b) a serotonin reuptake inhibitor (e.g., sertraline, fluoxetine, fluvoxamine, paroxetine, citalopram, fenfluramine, femoxetine, etc.) or a serotoin-1A ($5HT_{1A}$) receptor ligand (e.g., buspirone, flesinoxan, etc.) or a pharmaceutically acceptable salt of such inhibitor or ligand; and (c) a pharmaceutically acceptable carrier;

wherein the amounts of the compound of formula I and the serotonin reuptake inhibitor or $5HT_{1A}$ receptor ligand that are contained in such compostion are such that the combination of the two active ingredients is effective in treating such disorder or condition.

This invention also relates to a method for treating a disorder or condition, the treatment of which can effected or facilitated by modulating glutamate neurotransmission in a mammal, comprising administering to a mammal requiring such treatment:

(a) a glutamate neurotransmission modulating compound, or a pharmaceutically acceptable salt thereof; and (b) a serotonin reuptake inhibitor (es, sertraline, fluoxetine, fluvoxamine, paroxetine, citalopram, femoxetine, fenfluramine, etc.) or a serotonin-1A ($5HT_{1A}$) receptor ligand (e.g., buspirone, flesinoxan, etc.) or a pharmaceutically acceptable salt of such inhibitor or ligand;

wherein the amounts of the glutamate neurotransmission modulating compound and the serotonin reuptake inhibitor or $5HT_{1A}$ receptor ligand that are employed in such method are such that the combination of the two active ingredients is effective in treating such disorder or condition.

This invention also relates to a pharmaceutical composition for treating a disorder or condition, the treatment of which can effected or facilitated by modulating glutamate neurotransmission in a mammal, comprising:

(a) a glutamate neurotransmission modulating compound or a pharmaceutically acceptable salt thereof;

(b) a serotonin reuptake inhibitor (e.g., sertraline, fluoxetine, fluvoxamine, paroxetine, citalopram, fenfluramine, femoxetine, etc.) or a serotoin-1A ($5HT_{1A}$) receptor ligand (e.g., buspirone, flesinoxan, etc.) or a pharmaceutically acceptable salt of such inhibitor or ligand; and (c) a pharmaceutically acceptable carrier;

wherein the amounts of the glutamate neurotransmission modulating compound and the serotonin reuptake inhibitor or $5HT_{1A}$ receptor ligand that are contained in such compostion are such that the combination of the two active ingredients is effective in treating such disorder or condition.

This invention also relates to a method for treating a disorder or condition, selected from stroke, cerebral ischemia, spinal cord trauma, head trauma, Alzheimers Disease, Huntington's Chorea, amyotrophic lateral sclerosis, epilepsy, AIDS-induced dementia, muscular spasms, migraine headaches, urinary incontinence, psychosis, convulsions, perinatal hypoxia, hypoxia (such as conditions caused by strangulation, surgery, smoke inhalation, asphyxiation, drowning, choking, electrocution or drug or alcohol overdose), cardiac arrest, hypoglycemic neuronal damage, chemical dependencies and addictions (e.g., addictions to or dependencies on alcohol, opiates, benzodiazepines, nicotine, heroin or cocaine), ocular damage, retinopathy, retinal neuropathy, tinnitus, idiopathic and drug induced Parkinson's Disease, anxiety (e.g., panic disorder, Post Traumatic Stress Syndrome, General Anxiety Disorder, simple phobias and social phobias), schizophienia, depression, bipolar disorder, obsessive-compulsive disorder, Tourette's syndrome, emesis, brain edema, chronic and acute pain, tardive dyskinesia and cerebral deficits subsequent to cardiac bypass surgery and grafting in a mammal, comprising administering to a mammal requiring such treatment:

(a) a compound of the formula I, or a pharmaceutically acceptable salt thereof; and (b) a serotonin reuptake inhibitor (e.g., sertraline, fluoxetine, fluvoxamine, paroxetine, citalopram, fenfluramine, femoxetine, etc.) or a serotonin-1A ($5HT_{1A}$) receptor ligand (e.g., buspirone, flesinoxan, etc.) or a pharmaceutically acceptable salt of such inhibitor or ligand;

wherein the amounts of the compound of formula I and the serotonin reuptake inhibitor or $5HT_{1A}$ receptor ligand that are employed in such method are such that the combination of the two active ingredients is effective in treating such disorder or condition.

This invention also relates to a pharmaceutical composition for treating a disorder or condition selected from stroke, cerebral ischemia, spinal cord trauma, head trauma, Alzheimer's Disease, Huntington's Chorea, amyotrophic lateral sclerosis, epilepsy, AIDS-induced dementia, muscular spasms, migraine headaches, urinary incontinence, psychosis, convulsions, perinatal hypoxia, hypoxia (such as conditions caused by strangulation, surgery, smoke inhalation, asphyxiation, drowning, choking, electrocution or drug or alcohol overdose), cardiac arrest, hypoglycemic neuronal damage, chemical dependencies and addictions (e.g., addictions to or dependencies on alcohol, opiates, benzodiazepines, nicotine, heroin or cocaine), ocular damage, retinopathy, retinal neuropathy, tinnitus, idiopathic and drug induced Parkinson's Disease, anxiety (e.g., panic disorder, Post Traumatic Stress Syndrome, General Anxiety Disorder, simple phobias and social phobias), schizophienia, depression, bipolar disorder, obsessive-compulsive disorder, Tourette's syndrome, emesis, brain edema, chronic and acute pain, tardive dyskinesia and cerebral deficits subsequent to cardiac bypass surgery and grafting in a mammal, comprising:

(a) a compound of the formula I, or a pharmaceutically acceptable salt thereof; and (b) a serotonin reuptake inhibitor (e.g., sertraline, fluoxetine, fluvoxamine, citalopram, paroxetine, fenfluramine, femoxetine, etc.) or a serotoin-1A ($5HT_{1A}$) receptor ligand (e.g., buspirone, flesinoxan, etc.) or a pharmaceutically acceptable salt of such inhibitor or ligand; and (c) a pharmaceutically acceptable carrier;

wherein the amounts of the compound of formula I and the serotonin reuptake inhibitor or $5HT_{1A}$ receptor ligand that are contained in such composition are such that the combination of the two active ingredients is effective in treating such disorder or condition.

Unless otherwise indicated, the alkyl groups referred to herein, as well as the alkyl moieties of other groups referred to herein (e.g., alkoxy), may be linear or branched (e.g., t-butyl), and they may also be cyclic (e.g., cyclopropyl, cyclobutyl, cyclopentyl, or cyclohexyl) or be linear or branched and contain cyclic moieties.

The term "treating" as used herein, refers to reversing, alleviating, inhibiting the progress of, or preventing the disorder or condition to which such term applies, or one or more symptoms of such disorder or condition. The term "treatment", as used herein, refers to the act of treating, as "treating" is defined immediately above.

Unless otherwise indicated, "halo" and "halogen", as used herein, refer to fluorine, bromine, chlorine or iodine.

Compounds of the formula I may have chiral centers and therefore may exist in different enantiomeric and diastereomic forms. This invention relates to all optical isomers and all other stereoisomers of compounds of the formula 1, and to all racemic and other mixtures thereof, and to all pharmaceutical compositions and methods of treatment defined above that contain or employ such isomers or mixtures.

The subject invention also includes isotopically-labelled compounds, which are identical to those recited in formula 1, but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorous, fluorine and chlorine, such as $^2H$, $^3H$, $^{13}C$, $^{14}C$, $^{15}N$, $^{18})$, $^{17}O$, $^{31}P$, $^{32}P$, $^{35}S$, $^{18}F$, and $^{36}Cl$, respectively. Compounds of the present invention and pharmaceutically acceptable salts of said compounds which contain the aforementioned isotopes and/or other isotopes of other atoms are within the scope of this invention. Certain isotopically-labelled compounds of the present invention, for example those into which radioactive isotopes such as $^3H$ and $^{14}C$ are incorporated, are useful in drug and/or substrate tissue distribution assays. Tritiated, i.e., $^3H$, and carbon-14, i.e., $^{14}C$, isotopes are particularly preferred for their ease of preparation and detectability. Further, substitution with heavier isotopes such as deuterium, i.e., $^2H$, can afford certain therapeutic advantages resulting from greater metabolic stability, for example increased in vivo half-life or reduced dosage requirements and, hence, may be preferred in some circumstances. Isotopically labelled compounds of formula I of this invention can generally be prepared by carrying out the procedures disclosed in the Schemes and/or in the Examples and Preparations below, by substituting a readily available isotopically labelled reagent for a non-isotopically labelled reagent.

DETAILED DESCRIPTION OF THE INVENTION

The compounds of formula I can be prepared according to the methods of Scheme 1. In the reaction Scheme and discussion that follow, unless otherwise indicated, n, X, Z, $R^1$, $R^2$, and $R^7$ and structural formulas I, II, III and IV are defined as above.

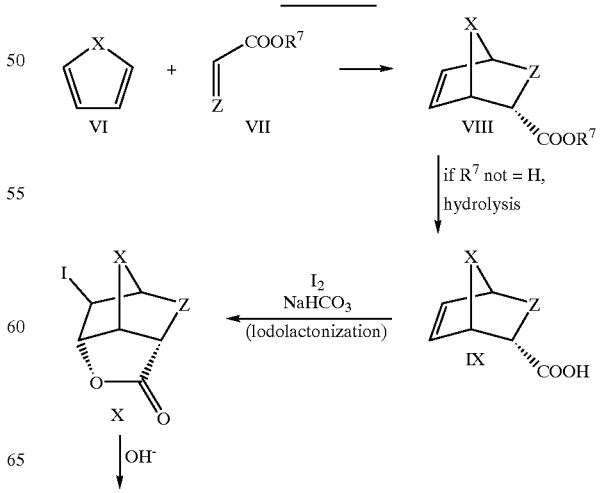

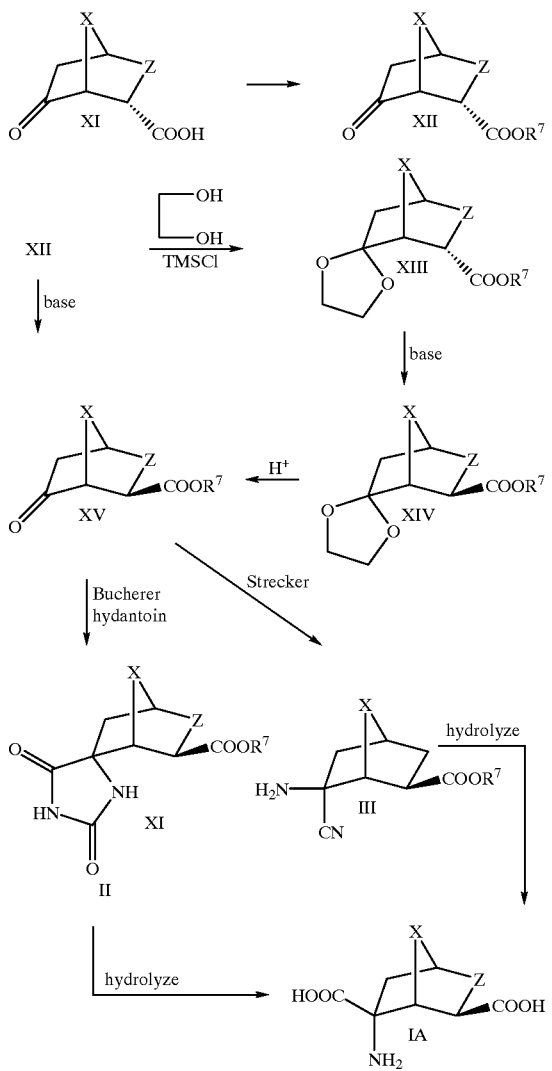

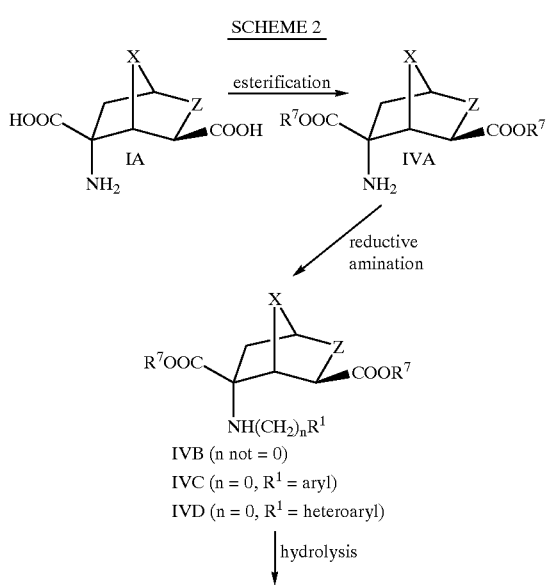

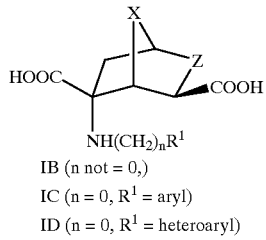

IB (n not = 0,)
IC (n = 0, $R^1$ = aryl)
ID (n = 0, $R^1$ = heteroaryl)

Scheme 1 illustrates the preparation of all compounds of the formula I wherein n is zero and $R^1$ is hydrogen. Such compounds are referred to in Scheme 1 and hereinafter as compounds of the formula IA. Referring to Scheme 1, a diene of the formula VI is reacted with a dienophile of the formula VII using the well known Diels Alder reaction. (See *Organic Reactions*, 1948, Vol IV, pp. 1–173). This reaction may be conducted in the absence of a solvent, or in any of a variety of solvents, including water, ether, tetrahydrofuran, benzene, toluene, and dichloroethane. It may be run at atmospheric pressure or in a closed vessel under 1–10 atmospheres of pressure. The reaction time will vary depending on the particular Diels Alder reaction. The reaction may occur upon admixing of the reagents or may require up to several days to complete. In the case where Z is $NR^2$, the starting material of formula VII may be formed in situ from the corresponding aldehyde wherein Z is oxygen and an amine of the formula $NH_2R^2$, and the reaction may be performed in water (*Tetrahedron Lett.*, 1990, 31, 2603; *J. Amer. Chem. Soc.*, 1985, 107, 1768–1769; *Bull. Chem. Soc. Japan*, 1992, 65, 61).

The Diels Alder reaction product of formula VII wherein $R^7$ is other than H may be hydrolyzed to the free acid using an aqueous acid such as hydrochloric acid (HCl), hydromoromic acid (HBr) or sulfuric acid ($H_2SO_4$), or using an aqueous hydroxide. A diluent such as tetrahydrofuran, methanol, ethanol or isopropanol may be added. The hydrolysis may be conducted at a temperature from about 0° C. to about 150° C., and is preferably conducted at a temperature from about room temperature to about 65° C.

The resulting compound of formula IX is further reacted with iodine and a base in an iodolactonization reaction (*J. Org. Chem.*, 1976, 41, 1229), to form the corresponding compound of formula X. This reaction is generally carried out in a solvent such as water, methanol, ether, or tetrahydrofuran, or mixtures of two or more of the foregoing solvents, and the base is generally an alkali metal bicarbonate. The reaction is typically conducted at a temperature from about 0° C. minutes to about 50° C., and is preferably conducted at about ambient temperature for a period of about 30 minutes to about 48 hours, usually for about 8 to 24 hours.

The iodolactone intermediate of formula X is then treated with a base, generally an alkali metal hydroxide in water, methanol or ethanol, or a mixture of two or more of these solvents, according to the procedure of Bastiaansen (*J. Org. Chem.*, 1995, 60, 4240) to prepare the corresponding intermediate having formula XI.

The compound of formula XI is then esterfied according to standard conditions well known in the art (e.g., reaction with diazomethane or trimethylsilyldiazomethane, or with trimethylsilyl chloride and an alcohol, or with an acid such as hydrochloric or sulfuric acid and an alcohol, or with a chloroformate such as methyl, ethyl or benzyl chloroformate.

The ketone of the resulting ketoester of formula XII may be protected as a ketal by treatment with ethylene glycol or an orthoformate such as trimethylorthoformate, under dehydrating conditions such as molecular seives or azeotropic removal of water, to produce the protected intermediate of formula XIII. A catalyst such as trimethylsilyl chloride, or an acid such as para-toluenesulfonic acid, sulfuric acid or benzenesulfonic acid, or pyridinium tosylate may be employed to facilitate this reaction. The reaction temperature can range from about ambient temperature to about the reflux temperature of the solvent. Suitable solvents include aprotic solvents such as toluene, benzene, tetrahydrofuran, dimethoxyethane, methylene chloride and dichloroethane. Treatment of the keto ester (XII) or the ketal ester (XIII) with a base such as sodium methoxide or sodium ethoxide, in an alcoholic solvent, at a temperature from about ambient temperature to about the reflux temperature of the solvent, from about 6 hours to about 5 days, equilibrates the ester predominantly into the exo position. Deketalization with an acid such as hydrochloric, sulfuric, oxalic, or acetic acid in water, alone or admixed with methanol, tetrahydrofuran or ether, affords the intermediate of formula XV.

The compound of formula XV is further reacted under Bucherer hydantoin forming conditions (See *J. Org. Chem.,* 1982, 47, 4081 and the references cited therein; Vogel's *Textbook of Practical Organic Chemistry,* 4th Ed., 1978, p. 876) to afford the hydantoin intermediate of formula XI. Such conditions include for example, reaction with an alkali metal cyanide and ammonium carbonate in water, methanol or ethanol, at a temperature from about ambient temperature to about 150° C., and a pressure from about ambient pressure to about 150 psi, for about 30 minutes to about 48 hours. Hydrolysis of the resulting hydantoin using a mineral acid or aqueous alkali metal hydroxide or aqueous barium hydroxide, generally at temperatures from about 50° C. to about 150° C., affords the desired final product of formula IA.

Alternatively, the compound of formula XV can be reacted under Strecker synthesis conditions (Jerry March, *Advanced Organic Chemistry,* 4th Ed, 1992, p. 965; Vogel, *Textbook of Practical Organic Chemistry* 4th Ed., 1978, p. 546) to prepare the alpha amino nitrile intermediate of formula 11. Such conditions include, for example, using either (a) ammonia and hydrogen cyanide, (b) ammonium cyanide, (c) an alkali metal cyanide and ammonium chloride, or (d) trimethylsilyl cyanide, in an alcoholic solvent such as methanol or ethanol, optionally adding an acid such as acetic acid, at a temperature from about 20° C. to about 100° C., for about 0.5 to about 24 hours, generally at a temperature between about 40° C. and 80° C. for about 1–8 hours. Hydrolysis of this intermediate, as described above for hydrolysis of the hydantoin, affords the desired final product of formula IA.

As illustrated in Scheme 2, compounds of formula IA may be esterified to form the corresponding diesters of formula IVA using the standard conditions described above. The resulting diesters containing a free amino group may be further functionalized on the amino group by standard reductive amination procedures to form the corresponding compounds of formulas IVB (n is not zero), IVC (n is zero and $R^1$ is aryl) and IVD (n is zero and $R^1$ is heteroaryl). When there is an alkyl linkage of $R^1$ to the amino nitrogen of formula I, i.e., n is not zero, a compound of the formula IVA is reacted with the appropriate aldehyde of the formula $R^1(CH_2)_m CHO$, wherein m is equal to n–1 (i.e., m is one less than n) to form a compound of the formula IVB. The above reductive amination reaction can be carried out using standard methods well known to those of skill in the art. This reaction is typically carried out in the presence of a reducing agent such as sodium cyanoborohydride, sodium triacetoxyborohydride, sodium borohydride, hydrogen (or a chemical hydrogen source such as formic acid or ammonium formate) and a metal catalyst such as platinum, palladium or rhodium, zinc and hydrochloric acid, borane dimethylsulfide or formic acid, at a temperature from about –60° C. to about 50° C. Suitable reaction inert solvents for this reaction include lower alcohols (e.g., methanol, ethanol and isopropanol), dioxane, methylene chloride, dichloroethane, acetic acid and tetrahydrofuran (THF). Preferably, the solvent is methylene chloride or dichloroethane, the temperature is about 25° C., and the reducing agent is sodium triacetoxyborohydride.

Compounds of the formula IVC and IVD are compounds identical to those of formula IVB except that n is zero and $R^1$ is aryl or heteroaryl, respectively. Such compounds can also be formed from the corresponding compounds of the formula IVA. This is accomplished by reacting the corresponding compounds of the formula IVA with a compound of the formula $R^1X$, wherein X is a leaving group such as halo, triflate, mesylate or tosylate. This reaction is generally carried out in a solvent such as ethanol, N,N-dimethylformamide (DMF), N,N-dimethylacetamide, acetonitrile, nitromethene, dioxane or dichloroethane, preferably DMF, at a temperature from about 0° C. to about 160° C., preferably from about 80° C. to about 150° C.

In an analogous fashion, compounds of the formula IVD can be prepared by reacting the corresponding compound of formula IVA with a heteroaromatic compound of the formula AX, wherein A is a nitrogen containing heterocycle and X is a leaving group, as defined above, which is ortho to a ring nitrogen. Examples of compounds of the formula AX are the following:

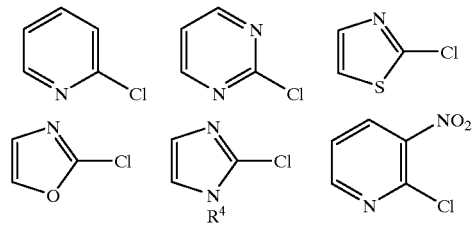

The presence on the above heteroaryl groups of electron withdrawing groups, for example esters, nitrites, sulfones, and nitro groups, further activates them.

The compounds of formulas IVB, IVC and IVD formed in the above reaction can be converted onto the corresponding desired compounds of formulas IB, IC and ID by subjecting them to acid or base hydrolysis, using methods well known to those of skill in the art. Suitable acids for the use in acid hydrolysis of compounds of the formula IVB include mineral acids such as hydrofluoric acid, sulfuric acid, hydrochloric acid and hydrobromic acid. Suitable bases for use in base hydrolysis of compounds of the formula IVB include alkali metal hydroxides and barium hydroxide. The reaction temperature for the acid and base hydrolysis reactions can range from about 0° C. to about 100° C. Preferably, these reactions are carried out at about the reflux temperature of the reaction mixture.

Additional compounds of the formula IC or ID, wherein $R^1$ is substituted aryl or heteroaryl, respectively, may be obtained from compounds of the formula IC or ID wherein $R^1$ is a nitroaryl or nitroheteroraryl group, respectively, by employing well known synthetic chemical methods. For example, following procedures such as those described by Jerry March, *Advanced Organic Chemistry*, 4th edition, pp. 721–725 and 1216–1217, the nitro group can be reduced to an amine. The newly formed amine can be replaced with other substituents by diazotization and further reaction as summarized in the above reference. For example, compounds of the formula I wherein $R^1$ is an aryl or heteroaryl group substituted with amino, mercapto, halo, cyano, or phenyl can be prepared in this manner.

The starting materials of formulas VI and VII, and those of formulas $R^1X$ and AX, are either commerically available, known in the literature, or readily obtainable from commercially available or known compounds using methods that are known in the art.

Unless indicated otherwise, the pressure of each of the above reactions is not critical. Generally, the reactions will be conducted at a pressure of about one to about three atmospheres, preferably at ambient pressure (about one atmosphere).

The preparation of other compounds of the formula I not specifically described in the foregoing experimental section can be accomplished using combinations of the reactions described above that will be apparent to those skilled in the art.

The compounds of the formula I that are basic in nature are capable of forming a wide variety of different salts with various inorganic and organic acids. The acid that can be used to prepare the pharmaceutically acceptable acid addition salts of the base compounds of this invention are those which form non-toxic acid addition salts, i.e., salts containing pharmacologically acceptable anions, such as hydrochloride, hydrobromide, hydroiodide, nitrate, sulfate or bisulfate, phosphate or acid phosphate, acetate, lactate, citrate or acid citrate, tartrate or bitartrate, succinate, maleate, fumarate, gluconate, saccharate, benzoate, methanesulfonate and pamoate [i.e., 1,1'-methylene-bis-(2-hydroxy-3-naphthoate)] salts. Although such salts must be pharmaceutically acceptable for administration to animals, it is often desirable in practice to initially isolate a compound of the formula I from the reaction mixture as a pharmaceutically unacceptable salt and then simply convert the latter back to the free base compound by treatment with an alkaline reagent, and subsequently convert the free base to a pharmaceutically acceptable acid addition salt. The acid addition salts of the base compounds of this invention are readily prepared by treating the base compound with a substantially equivalent amount of the chosen mineral or organic acid in an aqueous solvent medium or in a suitable organic solvent such as methanol or ethanol. Upon careful evaporation of the solvent, the desired solid salt is obtained.

Compounds of the formula that are acidic in nature are capable of forming base salts with various pharmacologically acceptable cations. These salts are all prepared by conventional techniques. The chemical bases that are used as reagents to prepare the pharmaceutically acceptable base salts of this invention are those which form non-toxic base salts with the acidic compounds of formula I. Such non-toxic base salts include those derived from such pharmacologically acceptable cations as sodium, potassium, calcium and magnesium, etc. These salts can easily be prepared by treating the corresponding acidic compounds with an aqueous solution containing the desired pharmacologically acceptable cations, and then evaporating the resulting solution to dryness, preferably under reduced pressure. Alternatively, they may also be prepared by mixing lower alkanolic solutions of the acidic compounds and the desired alkali metal alkoxide together, and then evaporating the resulting solution to dryness in the same manner as before. In either case, stoichiometric quantities of reagents are preferably employed in order to ensure completeness of reaction and maximum yields of the desired final product.

The compounds of the formula I and the pharmaceutically acceptable salts thereof (hereinafter, also referred to, collectively, as "the active compounds of the invention") are useful for the treatment of neurodegenerative, psychotropic and drug or alcohol induced deficits and are potent metabotropic glutamate receptor ligands antagonists. The active compounds of the invention may therefore be used in the treatment or prevention of stroke, cerebral ischemia, spinal cord trauma, head trauma, Alzheimers Disease, Huntington's Chorea, amyotrophic lateral sclerosis, epilepsy, AIDS-induced dementia, muscular spasms, migraine headaches, urinary incontinence, psychosis, convulsions, perinatal hypoxia, hypoxia (such as conditions caused by strangulation, surgery, smoke inhalation, asphyxiation, drowning, choking, electrocution or drug or alcohol overdose), cardiac arrest, hypoglycemic neuronal damage, chemical dependencies and addictions (e.g., addictions to or dependencies on alcohol, opiates, benzodiazepines, nicotine, heroin or cocaine), ocular damage, retinopathy, retinal neuropathy, tinnitus, idiopathic and drug induced Parkinson's Disease, anxiety, emesis, brain edema, chronic and acute pain, tardive dyskinesia and cerebral deficits subsequent to cardiac bypass surgery and grafting.

The following procedure can be used to determine the activity of the therapeutic agents of this invention as agonists and as antagonists of metabotropic glutamate receptors.

Chinese hamster ovary (CHO) cells were transfected with cDNA (mGluR2 and pcDNA3) using a calcium-phosphate method. Positive clones were selected for using geneticin (G418, Gibco, 500–700 $\mu$g/ml), and analyzed with RT-PCR for the presence of mGluR2 mRNA (primers for mGluR2: 5'-AAG TGC CCG GAG MC TTC MC GAA-3' AND 5'-AAA GCG ACG ACG TTG TTG AGT CCA-3'). Positive clones were grown to confluency and cAMP responses were measured in the presence of 10AlM forskolin. Confluent clones were frozen and stored in liquid nitrogen.

Chinese hamster ovary (CHO) cells stably transfected with the rat metabotropic glutamate receptor, mGluR2, were grown to confluence in Dulbecco's Modified Eagle Medium (DMEM) (Gibco catalog # 11960-044), containing 10% dialysed fetal bovine serum, 1% proline, 0.11 mg/ml sodium pyruvate, 0.5 mg/ml Geneticin, 2 mM I-glutamine, and penicillin/streptomycin. Cells were harvested using a 5 mM ethylenediaminetetraacetic acid (EDTA) solution, and then spun down at 800 rpm in a 4° C. refrigerated centrifuge. The remaining pellet was resuspended in a phosphate-buffered saline solution containing 30 mM HEPES (Giboo, catino.15630-080) 5 mM magnesium chloride ($MgCl_2$), 300 $\mu$M 3-Isobutyl-I-methylxanthine (IBMX), and 0.1% dextrose. The cell suspension was added in 200 pl aliquots to flat bottomed polypropylene tubes that were then placed in a 37° C. heated water bath for 22 minutes. If a compound was being tested for antagonist activity, it was allowed to pre-incubate with the cells in the bath during the first 11 minutes. At the end of the 11 minutes, 5 $\mu$M forskolin plus a known concentration of an test compound were added, and the incubation was continued for another 11 minutes. If a compound was being tested for agonist activity, the cells were allowed to shake in the bath for the initial 11 minutes, and then 5 $\mu$M forskolin plus a known concentration of agonist were added for the remaining 11 minute incubation. In either case, the reaction was stopped with 25 $\mu$l of 6N perchloric acid (PCA), and each tube was transferred immediately to an ice water bath. The pH of each sample was adjusted to approximately 8.0 with the addition of potassium hydroxide (KOH), and stabilized with the addition of Tris, pH 7.4. Aliquots (25 µl) were assayed in a commercial competitive binding kit (Amersham TRK.432). The samples were then harvested onto GF/B filters coated in 0.5% PEI using a 96-well Skatron harvester. Samples were quantified using a 1205 Betaplate liquid scintillation counter.

CPMs from the Betaplate reader were converted to pmoles cAMP/mg protein/minute of incubation with forskolin using an Excel spreadsheet. $EC_{50}$'s and $IC_{50}$'s can be calculated from linear regression of the concentration response data.

The following proceeding can be used to determine the agonist activity of the therapeutic agents of this invention as agonists of metabotropic glutamate receptors.

Chinese hamster ovary (CHO) cells stably transfected with the rat metabotropic glutamate receptor, mGluR2, were grown to confluence in DMEM (Gibco catalog # 11960-044), containing 10% dialyzed fetal bovine serum, 1% proline, 0.11 mg/ml sodium pyruvate, 0.5 mg/ml Geneticin, 2 mM 1-glutamine, and penicillin/streptomycin. Cells are harvested using a 5 mM EDTA solution, and homogenized for 10 strokes with a glass-teflon hand held homogenizer, then 50 volumes of a phosphate buffered saline solution (PBS) are added and the solution is spun at 18,000 RPM for 10 minutes at 4° C. The pellet is rehomogenized and resuspended in assay buffer (100 mM HEPES, 1 mM EGTA, pH 7.5) at a concentration that will result in approx. 0.009 mg protein/well. A reaction mix containing 6mM $MgCl_2$, 0.5 mM adenosine triphosphate (ATP), 0.5 mM 3-isobutyl-1-methylxanthine (IBMX), 0.1 mM guanosine triphosphate (GTP), 10 mM phosphocreatine, 0.31 mg/ml creatine phosphokinase (final concentrations in assay) is prepared just prior to the initiation of the experiment. 20 µl of test compound, 20 µl of forskolin (5 µM final), 20 µl of reaction mix, and 40 µl of tissue are added in consecutive order to a 96-well polypropaline plate. The plate is incubated at 37° C. in a heated water bath for 15 minutes. The reaction is stopped with the addition of 50 µl of 40 mM EDTA. The plate is then transferred to ice and shaken for 10–15 minutes before a 25 µl aliquot is removed for analysis in a commercial competitive binding kit (Amersham TRK.432). After a 2–18 hour incubation in the refrigerator, the samples are harvested onto GF/B filters coated in 0.5% polyethylenimine (PEI) using a 96-well Skatron harvester. Samples were quantified using a 1205 Betaplate liquid scintillation counter.

CPMs from the Betaplate reader are converted to pmoles cAMP/well using an Excel spreadsheet. Agonist compounds are identified by percent reduction of the forskolin signal, also in Excel. $EC_{50}$'s are calculated from linear regression of the concentration response data.

The compositions of the present invention may be formulated in a conventional manner using one or more pharmaceutically acceptable carriers. Thus, the active compounds of the invention may be formulated for oral, buccal, transdermal (e.g., patch), intranasal, parenteral (e.g., intravenous, intramuscular or subcutaneous) or rectal administration or in a form suitable for administration by inhalation or insulation.

For oral administration, the pharmaceutical compositions may take the form of, for example, tablets or capsules prepared by conventional means with pharmaceutically acceptable excipients such as binding agents (e.g., pregelatinised maize starch, polyvinylpyrrolidone or hydroxypropyl methylcellulose); fillers (e.g., lactose, microcrystalline cellulose or calcium phosphate); lubricants (e.g., magnesium stearate, talc or silica); disintegrants (eg, potato starch or sodium starch glycollate); or wetting agents (e.g., sodium lauryl sulphate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (e.g., sorbitol syrup, methyl cellulose or hydrogenated edible fats); emulsifying agents (e.g., lecithin or acacia); non-aqueous vehicles (e.g., almond oil, oily esters or ethyl alcohol); and preservatives (e.g., methyl or propyl p-hydroxybenzoates or sorbic acid).

For buccal administration the composition may take the form of tablets or lozenges formulated in conventional manner.

The active compounds of the invention may be formulated for parenteral administration by injection, including using conventional catheterization techniques or infusion. Formulations for injection may be presented in unit dosage form, e.g., in ampules or in multi-dose containers, with an added preservative. The compositions may take such forms as suspensions, solutions or emulsions in oily or aqueous vehicles, and may contain formulating agents such as suspending, stabilizing and/or dispersing agents. Alternatively, the active ingredient may be in powder form for reconstitution with a suitable vehicle, e.g., sterile pyrogen-free water, before use.

The active compounds of the invention may also be formulated in rectal compositions such as suppositories or retention enemas, e.g., containing conventional suppository bases such as cocoa butter or other glycerides.

For intranasal administration or administration by inhalation, the active compounds of the invention are conveniently delivered in the form of a solution or suspension from a pump spray container that is squeezed or pumped by the patient or as an aerosol spray presentation from a pressurized container or a nebulizer, with the use of a suitable propellant, e.g., dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount. The pressurized container or nebulizer may contain a solution or suspension of the active compound. Capsules and cartridges (made, for example, from gelatin) for use in an inhaler or insufflator may be formulated containing a powder mix of a compound of the invention and a suitable powder base such as lactose or starch.

A proposed dose of the active compounds of the invention for oral, parenteral or buccal administration to the average adult human for the treatment of the conditions referred to above (e.g., stroke) is 0.01 to 50 mg/kg of the active ingredient per unit dose which could be administered, for example, 1 to 4 times per day.

Aerosol formulations for treatment of the conditions referred to above (e.g., stroke) in the average adult human are preferably arranged so that each metered dose or "puff" of aerosol contains 20 mg to 1000 mg of the compound of the invention. The overall daily dose with an aerosol will be within the range 100 mg to 10 mg. Administration may be several times daily, for example 2, 3, 4 or 8 times, giving for example, 1, 2 or 3 doses each time.

The following Examples illustrate the preparation of the compounds of the present invention. Commercial reagents were utilized without further purification. Melting points are uncorrected. All NMR data were recorded at 250, 300 or 400 MHz in deuterochloroform unless otherwise specified and are reported in parts per million (6) and are referenced to the deuterium lock signal from the sample solvent. All non-aqueous reactions were carried out in dry glassware with dry solvents under an inert atmosphere for convenience and to maximize yields. All reactions were stirred with a magnetic stirring bar unless otherwise stated. Unless otherwise stated, all mass spectra were obtained using chemical impact conditions. Ambient or room temperature refers to 20–25° C. Melting points are uncorrected.

The following Examples 1–4 are examples of compounds of formula 1. These Examples are provided to merely illustrate aspects of the subject invention. They are not intended and should not be construed to limit the invention set forth in the claims and more fully described herein.

EXAMPLE 1

2-(Endo)-Amino-Bicyclo [2.2.1] Heptane-2-(Exo), 6-(Exo)-Dicarboxylic Acid

A. Methyl bicyclo [2.2.1] heptan-2-one-6-carboxylate

Hydantoin (85-15 mixture of endo:exo hydantoin nitrogen

To a mixture of methyl bicyclo[2.2.1]heptan-2-one-6-exo-carboxylate (0.557 g, 3.31 mmol, J. Org. Chem., 1995, 60, 4240–4245) and ammonium carbonate (1.6 g, 16.65 mmol) in water (9 mL) and methanol (9 mL) was added potassium cyanide (0.456 g, 7 mmol). The mixture was warmed to 41.5° C. and stirred overnight. The mixture was diluted with water and repeatedly extracted with ethyl acetate. The combined ogranic phase was washed with water, dried over magnesium sulfate, and concentrated to afford a white solid. This solid was flash chromatographed on silica gel (40×80 mm) with elution proceeding as follows: 50% ethyl acetate/hexane, 112 mL, nil; 42 mL, unidentified impurity; 322 mL, nil; 322 mL, 0.299 g of title product as a white solid which had: $^1$H NMR (CDCl$_3$) (major diastereomer with endo hydantoin nitrogen) δ 10.60 (s, 1H), 8.23 (s, 1H), 3.55 (s, 3H), 2.81 (q, J=4.5 Hz, 1H), 2.42 (s, 1H), 2.26 (s, 1H), 2.04 (d, J=10.1 Hz, 1H), 1.92 (dt, J=3.5, 12.25 Hz, 1H), 1.84–1.76 (m, 1H), 1.60–1.52 (m, 1H), 1.30 (d, J=10.1 Hz, 1H), 1.20 (d, J=12.7 Hz, 1H).

B. (endo) Amino-bicyclo[2.2.1]heptane-2,6 di (exo) carboxylic acid

A mixture of methyl bicyclo [2.2.1] heptan-2-one-6-exo-carboxylate hydantoin (0.10 g, 0.41 mmol) in 6N hydrochloric acid (10 mL) was refluxed 24 hours, cooled and allowed to stand at ambient temperature 72 hours. The reaction was concentrated to a white solid in vacuo. The solid was dissolved in water with the aid of 2 drops of 6 N hydrochloric acid and applied to a Dowex 50 x8 100 ion exchange column (7 mL of resin prepared by eluting with water until the eluent pH=4). The column was eluted with water until the pH reached 4.5. Elution was continued with 1 N ammonium hydroxide. Ninhydrin positive fractions were combined and lyophilized to afford 0.032 g of white solid product which had: $^1$H NMR (D$_2$O) δ 2.53 (s, 1H), 2.30–2.22 (m, 1H), 2.20–2.16 (br s, 1H), 2.12–2.04 (m, 1H), 1.75 (d, J=11.8 Hz, 1H), 1.72–1.64 (m, 1H), 1.52–1.44 (m, 1H), 1.28–1.20 (m, 1H), 1.08 (dd, J=2.7, 13.5 Hz, 1H), APCI MS m/e=200.2 (P+1).

EXAMPLE 2

(+)-2-(endo)-Amino-bicyclo [2.2.1] heptane-2-(exo), 6-(exo)-dicarboxylic acid hydrochloride and (−)-2-(endo)-Amino-bicyclo [2.2.1] heptane-2-(exo), 6-(exo)-dicarboxylic acid hydrochloride A. Bicyclo [2.2.1] heptan-2-one-6-carboxylic acid hydantoin A solution of methyl bicyclo [2.2.1] heptan-2-one-6-exo-carboxylate hydantoin (1.02 g, 4.28 mmol) in 6 N hydrochloric acid (20 mL) was refluxed 1 hour. Upon cooling to ambient temperature the white solid product precipitated. The solid was collected and air dried to afford 0.776 g of title product which had: $^1$H NMR (D$_2$O) δ 2.65 (br s, 1H), 2.56 (s, 1H), 2.25 (s, 1H), 2.02–1.83 (m, 2H), 1.82–1.72 (m, 1H), 1.58–1.46 (distorted t, 1H), 1.34–1.19 (distorted t, 2H).

B. Resolution of bicyclo [2.2.1] heptan-2-one-6-exo-carboxylic acid hydantoin

Bicyclo [2.2.1] heptan-2-one-6-carboxylic acid hydantoin (0.776 g) was combined with methanol (20 mL) and (s)-(−)-α-methylbenzylamine (0.470 mL) was added. The mixture was stirred at ambient temperature for 2 hours. During this time the solution became homogeneous and then a white precipitate formed. The precipitate was collected (0.50 g) and recrystallized twice from methanol. The recrystallized salt was treated with 1 N hydrochloric acid and extracted repeatedly with ethyl acetate. The combined organic layer was dried over magnesium sulfate and concentrated to afford 0.120 g of the (−) enantiomer of bicyclo [2.2.1] heptan-2-one-6-carboxylic acid hydantoin which had an NMR spectrum identical to that of the racemic material and $[α]_D$=−36.11° (c=0.925 methanol). Chiral HPLC analysis (chiralcel OG column, 95/5 hexane/ethanol with 0.1% trifluoroacetic acid solvent, flow rate=1 mL/min, 214 nM UV detection) showed the compound to be 100% enantiomerically pure with a retention time of 14.50 min.

The mother liquors from the salt resolution above were combined and treated with 1 N hydrochloric acid. Repeated extraction with ethyl acetate allowed the recovery of bicyclo [2.2.1] heptan-2-one-6-carboxylic acid hydantoin enriched in the (+) enantiomer. This material was treated with (R)-(+)-α-methylbenzylamine as above to afford 0.066 g of (+)-bicyclo [2.2.1] heptan-2-one-6-carboxylic acid hydantoin as a white solid which had: $[α]_D$32 +32.77° (c=0.900 methanol). Chiral HPLC according to the method above showed the sample to have an enantiomeric excess of 98.1% with a retentiom time of 17.56 min.

C. (+)-2-(endo)-Amino-bicyclo [2.2.1] heptane-2-(exo), 6-(exo)-dicarboxylic acid hydrochloride (+)-Bicyclo [2.2.1] heptan-2-one-6-carboxylic acid hydantoin (0.098 g, 0.4 mmol) was combined with 6 N hydrochloric acid (20 mL) and refluxed for 48 hours. The mixture was concentrated in vacuo to afford 0.095 g of title product which had: $[α]_D$=+20.31° (c=1.07 methanol).

D. (−)-2-(endo)-Amino-bicyclo [2.2.1] heptane-2-(exo), 6-(exo)-dicarboxylic acid hydrochloride Using the same hydrolysis procedure described above, (−)-bicyclo [2.2.1] heptan-2-one-6-carboxylic acid hydantoin was converted to the (−) title product which had: $[α]_D$=−24.06° (c=0.575 methanol).

EXAMPLE 3

2-(Endo)-benzylamino-bicyclo[2.2.1]heptane-2-(exo)-6-(exo)-dicarboxylic acid

A. Dimethyl 2-(endo)-benzylamino-bicyclo[2.2.1] heptane-2-(exo)-6-(exo)-dicarboxylate A mixture of dimethyl 2-(endo)-amino-bicyclo[2.2.1]heptane-2-(exo)-6(exo)-dicarboxylate (0.25 g, 1.1 mmol) (see Preparation 1, below), methylene chloride (10 mL), benzaldehyde (0.134 mL), and sodium triacetoxyborohydride (1.2 g, 5.5 mmol) was stirred 16 hours. The reaction was quenched with 0.5 N Hcl (20 mL) and stirred 30 minutes. The phases were separated and the organic layer was washed with saturated aqueous bicarbonate, water, and brine. The organic layer was dried over magnesium sulfate and concentrated to leave 0.225 g of colorless oil. This oil was chromatographed on silica gel (using a Flash 40s cartridge from Biotage (Charlottesville, Va., USA); the Flash 40s cartridge contains KP sil) with elution proceeding as follows: 10% ethyl acetatelhexane, 100 mL, nil; 100 mL, 0.043 g of dimethyl-2-(endo)-benzylamino-bicyclo[2.2.1]heptane-2-(exo)-6-(exo)-dicarboxylate as a colorless oil which had: NMR (CDCl$_3$) δ 7.31–7.29 (m, 5h), 3.73 (s, 3H), 3.66 (s, 3H),3.51 (ABq, δv$_{1-3}$=40 Hz, J=13 Hz, 2H), 3.32, (dd, J=5, 9 Hz, 1H), 2.95 (s, 1H), 2.28 (br s, 1H), 2.21–2.15 (m, 1H), 1.97–1.90 (m, 1H), 1.88 (s, 1H), 1.59–1.54 (m, 1H), 1.45 (ABq, δv$_{1-3}$=24 Hz, J=11 Hz, 2H), 1.10 (dd, J=3, 13 Hz, 1H).

B. Hydrolysis of ester groups

A mixture of dimethyl 2-(endo)-benzylamino-bicyclo[2.2.1]heptane-2-(exo)-6-(exo)-dicarboxylate (0.04 g, 0.126 mmol), obtained as described in the preceding paragraph (A), and 6 N HCl (5 mL) was warmed to 80° C. overnight. Additional 6 N HCI (5 mL) was added and the reaction was heated at 103° C. for 24 hours. The mixture was cooled and concentrated. NMR of the residue indicated that monohydrolysis had occurred. The residue was combined with water (5 mL) and ethanol (5 mL) and LiOH (0.15 g, 6.2 mmol) was added. The mixture was heated at 650 for 16 hours. The reaction was concentrated and most of the residual solid was taken up in ethanol. Residual solids were removed from the ethanol solution by filtration through celite. The ethanol filtrate was concentrated to afford 0.242 9 of off white solid. The solid was taken up in 1N HCl (1 mL) and applied to AG50w-x8 ion exchange resin (0.15 g which had been previously washed with water until the pH increased to 4.5). This mixture was stirred over the weekend. An SCX column (0.5 g, strong cation exchange, from Burdick and Jackson (Muskegon, Mich., USA) (catalog #9094) was prepared by flushing with water until the eluent pH was 4.5. The ion exchange resin and its associated solution were applied to the SCX column and eluted as follows: water, 3 mL, unknown material; water, 30 mL, nil; 1 N ammonium hydroxide, 28 mL, 0.02 g of title product of this Example as a white solid which had: NMR (D$_2$O) δ 7.23–7.15 (m, 5H), 3.32 (ABq, δv$_{1-3}$=20 Hz, J=12 Hz, 2H), 2.63 (s, 1H), 2.55 (dd, J=5, 9.5 Hz, 1H), 2.03 (s, 1h), 1.87–1.81 (br d, 1H), 1.58–1.51 (m, 1H), 1.41 (t, J=10.5 Hz, 1H), 1.26 (m, 2H), 0.88 (d, J=11.5 Hz, 1H); APCl MS, p+1=290.2.

EXAMPLE 4

2-(Endo)-phenylethylamino-bicyclo[2.2.1]heptane-2-(exo)-6-(exo)-dicarboxylic acid Following substantially the same procedure described for Example 3, above, but with a direct LiOH hydrolysis (without the acidic partial hydrolysis step), the title compound of the current Example was prepared from dimethyl 2-(endo)-aminobicyclo[2.2.1]heptane-2-(exo)-6-(exo)-dicarboxylate (0.015 9, 0.066 mmol), methylene chloride (2 mL), phenylacetaldehyde (0.01 mL, 0.08 mmol), and sodium triacetoxyborohydride (0.07 g, 0.33 mmol). The title compound of the current Example had: NMR (D$_2$O) δ 7.19–7.11 (m, 5H), 2.70–2.44 (m, 5H), 2.38 (dd, J=5, 9 Hz, 1H), 2.05–2.01 (m, 1H), 1.82 (ddd, J=3, 5, 13 Hz, 1H), 1.58–1.51 (m, 1H), 1.41 (t, J=10.5 Hz, 1H), 1.24–1.16 (m, 2H), 0.85 (dd, J=2, 11.5 Hz, 1H); APCl MS, p+1=304.1.

PREPARATION 1

Dimethyl 2-(endo)-amino-bicyclo[2.2.1]heptane-2-(exo)-6-(exo)-dicarboxylate hydrochloride 2 (Endo)-amino-bicyclo[2.2.1]heptane-2-(exo)—(exo)-dicarboxylic acid (0.010 g, 0.05 mmol) was dissolved in methanol (5 mL) and the solution was saturated with HCl gas. The mixture was heated under reflux overnight. The reaction was cooled and concentrated to afford the title compound of this Preparation as a white solid which had: NMR (CD$_3$OD) δ 3.84 (s, 3H), 3.68 (s, 3H), 2.90 (s, 1H), 2.74–2.62 (m, 1H), 2.54–2.40 (m, 2H), 2.06–1.96 (m, 1H), 1.88 (d, J=11 Hz, 1H), 1.84–1.74 (m, 1H), 1.52 (dd, J=4.5, 11 Hz, 1H), 1.34 (dd, J=1.9, 13.5 Hz, 1H).

PREPARATION 2

Diethyl 2-(endo)-amino-bicyclo[2.2.1]heptane-2-(exo)-dicarboxylate

The compound of this Preparation is also useful for preparing compounds of formula I. 2-(Endo)-amino-bicyclo[2.2.1]heptane-2-(exo)-6-(exo)-dicarboxylic acid (0.392 g, 1.96 mmol) was dissolved in ethanol (15 mL) and the solution was saturated with HCl gas. The mixture was heated under reflux overnight. the solution was concentrated and the residue was treated with saturated aqueous sodium bicarbonate. This aqueous mixture was further treated with sodium carbonate to bring the pH to 10. The aqueous layer was repeatedly extracted with ethyl acetate. The combined organic layer was dried over magnesium sulfate and concentrated to afford the pale yellow oil title compound of this Preparation which had: NMR (CDCL$_3$) δ 4.20–4.05 (m, 4H), 3.30 (dd, J=5, 8.5 Hz, 1H), 2.69 (s, 1H), 2.37 (ddd, J=3, 4.8, 13 Hz, 1H), 2.27 (s, 1H), 1.94–1.86 (m, 1H), 1.95–1.75 (br s, 2H), 1.55 (t, J=11 Hz, 1H), 1.42 (ABq, δv$_{1-3}$=23 Hz, J=11 Hz, 2H), 1.27–1.21 (m, 6H), 0.91 (dd, J=2, 13 Hz, 1H).

What is claimed is:

1. A compound of the formula

I wherein n is 0–6;

X is $CH_2$, $CH_2CH_2$ or oxygen;

Z is $CHR^2$ or $NR^2$;

$R^1$ and $R^2$ are selected independently from hydrogen, $(C_1–C_6)$alkyl, aryl and heteroaryl, wherein said aryl is selected from phenyl and naphthyl and said heteroaryl is selected from 5 and 6 membered aromatic heterocyclic rings that contain from one to four heteroatoms selected, independently, from nitrogen, oxygen and sulfur, and wherein said aryl and heteroaryl moieties can optionally be substituted with one or more substituents that are selected, independently, from halo, —S($C_1$–$C_6$)alkyl, —S(O)($C_1$–$C_6$)alkyl, —S(O)$_2$ ($C_1$–$C_6$)alkyl, ($C_1$–$C_6$)alkyl optionally substituted with from one to seven fluorine atoms, ($C_1$–$C_6$)alkoxy optionally substituted with from one to seven fluorine atoms, amino, nitro, cyano, carboxy, —CO$_2$($C_1$–$C_6$) alkyl, ($C_1$–$C_6$)alkylamino, di-[($C_1$–$C_6$)alkyl]amino phenoxy, anilino and phenylthio;

with the proviso that none of said heteroaryl moieties contains more than one ring oxygen atom or more than one ring sulfur atom;

or a pharmaceutically acceptable salt of such compound.

2. A compound according to claim 1 wherein Z is $CH_2$.

3. A compound according to claim 1 wherein $R^1$ is selected from the group consisting of hydrogen, unsubstituted phenyl, and phenyl substituted with one or two substituents.

4. A compound according to claim 1 wherein n is zero, 1 or 2.

5. A compound according to claim 1 wherein X is $CH_2$.

6. A compound according to claim 1 selected from the group consisting of:

2-(endo)-amino-bicyclo[2.2.1]heptane-2-(exo)-6-(exo)-dicarboxylic acid;

(+)-2-(endo)-aminobicyclo[2.2.1]heptane-2-(exo)-6-(exo)-dicarboxylic acid;

(−)-2-(endo)-aminobicyclo[2.2.1]heptane-2-(exo)-6-(exo)-dicarboxylic acid;

2-(endo)-benzylamino-bicyclo[2.2.1]heptane-2-(exo)-6-(exo)-dicarboxylic acid; and 2-(endo)-phenylethylamino-bicyclo[2.2.1]heptane-2-(exo)-6-(exo)-dicarboxylic acid.

7. A pharmaceutical composition for treating a disorder or condition selected from stroke, cerebral ischemia, spinal cord trauma, head trauma, Alzheimer's Disease, Huntington's Chorea, amyotrophic lateral sclerosis, AIDS-induced dementia, muscular spasms, migraine headaches, urinary incontinence, psychosis, convulsions, perinatal hypoxia, hypoxia, cardiac arrest, hypoglycemic neuronal damage, chemical dependencies and addictions, ocular damage and retinopathy, idiopathic and drug induced Parkinson's Disease, anxiety, including panic disorder, General Anxiety Disorder, Post Traumatic Stress Syndrome, simple phobias, and social phobia; schizophrenia, depression, bipolar disorder, obsessive-compulsive disorder, Tourette's syndrome, emesis, brain edema, chronic and acute pain, tardive dyskinesia and cerebral deficits subsequent to cardiac bypass surgery and grafting in a mammal, comprising an amount of a compound according to claim 1 that is effective in treating such disorder or condition and a pharmaceutically acceptable carrier.

8. A pharmaceutical composition for treating a disorder or condition, the treatment or prevention of which can be effected or facilitated by modulating glutamate neurotransmission in a mammal, comprising an amount of a compound according to claim 1 that is effective in treating such disorder or condition and a pharmaceutically acceptable carrier.

9. A method for treating a disorder or condition selected from stroke, cerebral ischemia, spinal cord trauma, head trauma, Alzheimer's Disease, Huntington's Chorea, amyotrophic lateral sclerosis, AIDS-induced dementia, muscular spasms, migraine headaches, urinary incontinence, psychosis, convulsions, perinatal hypoxia, hypoxia, cardiac arrest, hypoglycemic neuronal damage, opiate tolerance and withdrawal, ocular damage and retinopathy, idiopathic and drug induced Parkinson's Disease, anxiety, including panic disorder, General Anxiety disorder, Post Traumatic Stress Syndrome, simple phobias, and social phobia; schizophrenia, depression, bipolar disorder, obsessive-compulsive disorder, Tourefte's syndrome, emesis, brain edema, chronic and acute pain, tardive dyskinesia and cerebral deficits subsequent to cardiac bypass surgery and grafting, in a mammal, comprising administering to a mammal requiring such treatment an amount of a compound according to claim 1 that is effective in treating such condition.

10. A method for treating a disorder or condition, the treatment of which can be effected or facilitated by modulating glutamate neurotransmission in a mammal, comprising administering to a mammal requiring such treatment an amount of a compound according to claim 1 that is effective in treating such disorder or condition.

11. A pharmaceutical composition for treating a disorder or condition selected from stroke, cerebral ischemia, spinal cord trauma, head trauma, Alzheimer's Disease, Huntington's Chorea, amyotrophic lateral sclerosis, AIDS-induced dementia, muscular spasms, migraine headaches, urinary incontinence, psychosis, convulsions, perinatal hypoxia, cardiac arrest, hypoglycemic neuronal damage, opiate tolerance and withdrawal, ocular damage and retinopathy, idiopathic and drug induced Parkinson's Disease, anxiety, including panic disorder, General Anxiety Disorder, Post Traumatic Stress Syndrome, simple phobias, and social phobia, schizophrenia, depression, bipolar disorder, obsessive-compulsive disorder, Tourette's syndrome, emesis, brain edema, chronic and acute pain, tardive dyskinesia and cerebral deficits subsequent to cardiac bypass surgery and grafting, in a mammal, comprising a metabotropic glutamate neurotransmission modulating effective amount of a compound according to claim 1 and a pharmaceutically acceptable carrier.

12. A pharmaceutical composition for treating a disorder or condition, the treatment or prevention of which can be effected or facilitated by modulating glutamate neurotransmission in a mammal, comprising a metabotropic glutamate neurotransmission modulating effective amount of a compound according to claim 1 and a pharmaceutically acceptable carrier.

13. A method for treating a disorder or condition selected from stroke, cerebral ischemia, spinal cord trauma, head trauma, Alzheimers Disease, Huntington's Chorea, amyotrophic lateral sclerosis, AlDS-induced dementia, muscular spasms, migraine headaches, urinary incontinence, psychosis, convulsions, perinatal hypoxia, cardiac arrest, hypoglycemic neuronal damage, opiate tolerance and withdrawal, ocular damage and retinopathy, idiopathic and drug induced Parkinson's Disease, anxiety, including panic disorder, General Anxiety Disorder, Post Traumatic Stress Syndrome, simple phobias, and social phobia; schizophrenia, depression, bipolar disorder, obsessive-compulsive disorder, Tourette's syndrome, emesis, brain edema, chronic and acute pain, tardive dyskinesia and cerebral deficits subsequent to cardiac bypass surgery and grafting in a mammal, comprising administering to a mammal requiring such treatment a metabotropic glutamate neurotransmission modulating effective amount of a compound according to claim 1.

14. A method for treating a disorder or condition, the treatment or prevention of which can be effected or facilitated by reducing or inhibiting glutamate neurotransmission in a mammal, comprising administering to a mammal requiring such treatment a metabotropic glutamate neurotransmission modulating effective amount of a compound according to claim 1.

15. A pharmaceutical composition for treating a disorder or condition, the treatment of which can be effected or facilitated by modulating glutamate neurotransmission in a mammal, comprising:
(a) a compound of the formula I, or a pharmaceutically acceptable salt thereof;
(b) a serotonin reuptake inhibitor or a serotonin-1A (5HT$_{1A}$) receptor ligand, or a pharmaceutically acceptable salt of such inhibitor or ligand; and
(c) a pharmaceutically acceptable carrier;
wherein the amounts of the compound of formula I and the serotonin reuptake inhibitor or 5HT$_{1A}$ receptor ligand that are contained in such composition are such that the combination of the two active ingredients is effective in treating such disorder or condition.

16. A pharmaceutical composition according to claim 15, wherein (b) is a serotonin reuptake inhibitor selected from sertraline, fluoxetine, fluvoxamine, paroxetine, citalopram, fenfluramine, and femoxetine.

17. A method for treating a disorder or condition, the treatment of which can effected or facilitated by modulating glutamate neurotransmission in a mammal, comprising administering to a mammal requiring such treatment:
(a) a compound of the formula I, or a pharmaceutically acceptable salt thereof; and
(b) a serotonin reuptake inhibitor or a serotonin-1A (5HT$_{1A}$) receptor ligand, or a pharmaceutically acceptable salt of such inhibitor or ligand;
wherein the amounts of the compound of formula I and the serotonin reuptake inhibitor or 5HT$_{1A}$ receptor ligand that are employed in such method are such that the combination of the two active ingredients is effective in treating such disorder or condition.

18. A method according to claim 17, wherein (b) is a serotonin reuptake inhibitor selected from sertraline, fluoxetine, fluvoxamine, paroxetine, citalopram, fenfluramine, and femoxetine.

19. A pharmaceutical composition for treating a condition selected from stroke, cerebral ischemia, spinal cord trauma, head trauma, Alzheimers Disease, Huntington's Chorea, amyotrophic lateral sclerosis, AIDS-induced dementia, muscular spasms, migraine headaches, urinary incontinence, psychosis, convulsions, perinatal hypoxia, hypoxia, cardiac arrest, hypoglycemic neuronal damage, chemical dependencies and addictions, ocular damage and retinopathy, idiopathic and drug induced Parkinson's Disease, anxiety, including panic disorder, General Anxiety Disorder, Post Traumatic Stress Syndrome, simple phobias, and social phobia; schizophrenia, depression, bipolar disorder, obsessive-compulsive disorder, Tourette's syndrome, emesis, brain edema, chronic and acute pain, tardive dyskinesia and cerebral deficits subsequent to cardiac bypass surgery and grafting in a mammal, comprising:
(a) a compound according to claim 1 or a pharmaceutically acceptable salt thereof;
(b) a serotonin reuptake inhibitor or a 5HT$_{1A}$ receptor ligand, or a pharmaceutically acceptable salt of such inhibitor or ligand; and
(c) a pharmaceutically acceptable carrier;
wherein the compound according to claim 1 and the 5HT$_{1A}$ receptor ligand or serotonin reuptake inhibitor that are contained in such composition are present in amounts such that the combination of the two active ingredients is effective in treating such condition.

20. A pharmaceutical composition according to claim 19, wherein (b) is a serotonin reuptake inhibitor selected from sertraline, fluoxetine, fluvoxamine, paroxetine, citalopram, fenfluramine, and femoxetine.

21. A method for treating a condition selected from stroke, cerebral ischemia, spinal cord trauma, head trauma, Alzheimer's Disease, Huntington's Chorea, amyotrophic lateral sclerosis, AIDS-induced dementia, muscular spasms, migraine headaches, urinary incontinence, psychosis, convulsions, perinatal hypoxia, hypoxia, cardiac arrest, hypoglycemic neuronal damage, opiate tolerance and withdrawal, ocular damage and retinopathy, idiopathic and drug induced Parkinson's Disease, anxiety, including panic disorder, General Anxiety Disorder, Post Traumatic Stress Syndrome, simple phobias, and social phobia; schizophrenia, depression, bipolar disorder, obsessive-compulsive disorder, Tourette's syndrome, emesis, brain edema, chronic and acute pain, tardive dyskinesia and cerebral deficits subsequent to cardiac bypass surgery and grafting, in a mammal, comprising administering to a mammal requiring such treatment;
(a) a compound according to claim 1 or a pharmaceutically acceptable salt thereof; and
(b) a serotonin reuptake inhibitor or a 5HT$_{1A}$ receptor ligand, or a pharmaceutically acceptable salt of such inhibitor or ligand;
wherein the amounts of the compound according to claim 1 and the 5HT$_{1A}$ receptor ligand or serotonin reuptake inhibitor that are employed in such method are such that the combination of the two active ingredients is effective in treating such condition.

22. A method according to claim 21, wherein (b) is a serotonin reuptake inhibitor selected from sertraline, fluoxetine, fluvoxamine, paroxetine, citalopram, fenfluramine, and femoxetine.

23. A compound of the formula

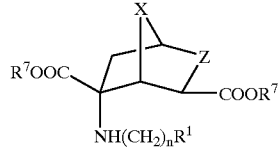

IV wherein n is 0–6;
X is CH$_2$, CH$_2$CH$_2$ or oxygen;
Z is CHR or NR$^2$;
R$^1$ and R$^2$ are selected independently from hydrogen, (C$_1$–C$_6$)alkyl, aryl and heteroaryl, wherein said aryl is selected from phenyl and naphthyl and said heteroaryl is selected from 5 and 6 membered aromatic heterocyclic rings that contain from one to four heteroatoms selected, independently, from nitrogen, oxygen and sulfur, and wherein said aryl and heteroaryl moieties can optionally be substituted with one or more substituents that are selected, independently, from halo, —S(C$_1$–C$_6$)alkyl, —S(O)(C$_1$–C$_6$)alkyl, —S(O)$_2$(C$_1$–C$_6$)alkyl, (C$_1$–C$_6$)alkyl optionally substituted with from one to seven fluorine atoms, (C$_1$–C$_6$)alkoxy optionally substituted with from one to seven fluorine atoms, amino, nitro, cyano, carboxy, —CO$_2$(C$_1$–C$_6$)alkyl, (C$_1$–C$_6$)alkylamino, di-[(C$_1$–C$_6$)alkyl]amino phenoxy, anilino and phenylthio; and
R$^7$ is hydrogen, (C$_1$–C$_6$)alkyl or benzyl
with the proviso that none of said heteroaryl moieties contains more than one ring oxygen atom or more than one ring sulfur atom.

* * * * *